United States Patent [19]

Hamlin

[11] Patent Number: 4,608,969

[45] Date of Patent: Sep. 2, 1986

[54] PORTABLE TRACTION APPARATUS

[76] Inventor: Jerry F. Hamlin, 874 Shirley La., Boulder City, Nev. 89005

[21] Appl. No.: 681,233

[22] Filed: Dec. 13, 1984

Related U.S. Application Data

[63] Continuation-in-part of Ser. No. 472,211, Mar. 4, 1983, abandoned.

[51] Int. Cl.[4] .......... A61F 5/00; A61H 1/00

[52] U.S. Cl. .......... 128/71; 128/73; 128/75

[58] Field of Search .......... 128/69, 70, 71, 72, 128/73, 74, 75

[56] References Cited

U.S. PATENT DOCUMENTS

| | | | |
|---|---|---|---|
| 620,318 | 2/1899 | Havner | 128/71 |
| 1,078,894 | 11/1913 | Ashby | 128/73 |
| 1,374,115 | 4/1921 | Roemer | 128/71 |
| 1,642,158 | 9/1927 | Kubista | 128/71 |
| 1,950,948 | 3/1934 | Murray | 128/72 |
| 2,377,940 | 6/1945 | Hughes | 128/71 |
| 2,593,675 | 4/1952 | Hastings | 128/71 |
| 2,787,262 | 4/1957 | Warner | 128/71 |
| 2,798,481 | 7/1957 | Matthews | 128/71 |
| 3,134,379 | 5/1964 | Nightingale | 128/75 |
| 3,640,272 | 2/1972 | Hussey | 128/33 |
| 4,356,816 | 11/1982 | Granberg | 128/71 |
| 4,466,427 | 8/1984 | Granberg | 128/71 |

FOREIGN PATENT DOCUMENTS

| | | | |
|---|---|---|---|
| 208883 | 1/1924 | United Kingdom | 128/71 |

*Primary Examiner*—Olyde I. Coughenouh
*Attorney, Agent, or Firm*—Harry M. Weiss & Associates

[57] ABSTRACT

A portable traction table in one embodiment, has two spaced base supports having guide rails therebetween along which a good carriage travels. A flat body-supporting panel mounts removable over the base. The user's feet are strapped into the foot carriage by means of a flexible belt which is cinched around the user's ankles by means of a long-handled clamp. A manually operated biasing mechanism, such as a hydraulic pump or a screw jack, is operated by the user to urge the foot carriage toward a forward portion of the apparatus.

6 Claims, 14 Drawing Figures

PORTABLE TRACTION APPARATUS

BACKGROUND OF THE INVENTION

This application is a continuation-in-part of application Ser. No. 472,211, filed on Mar. 4, 1983 now abandoned.

This invention relates to an apparatus designed for vertebral traction. More particularly, it relates to a portable traction device which is easy to store, inexpensive to manufacture, and can be easily operated by a single person without assistance.

Back pain is one of the most common ailments reported by the medical profession. While back pain may be caused by trauma, over-activity, improper lifting, arthritis, excessive sedentary periods, and many other causes, relief is often elusive. In many cases, people experiencing back pain obtain relief by stretching their spine, thereby relaxing the body muscles and easing tension on the discs and nerves connected to the spinal column. Various methods have been attempted for stretching the spinal column, including hanging the body by either the neck or feet, and allowing the force of gravity to stretch the spine. These remedies are not totally effective because the force of gravity may be insufficient to accomplish the necessary stretching, and because the positions which one must assume can be uncomfortable or even painful. Furthermore, suspension of the body from the head may result in excessive stretching forces in the neck area, and suspension of the body by the feet results in a flow of blood to the head which may be dangerous to some people. In addition, the forces placed on the spine by simple suspension of the body are not subject to careful control.

The use of traction tables which permit stretching of the spine through an actual pulling apart of the feet and head of a person has been known for many years. Most traction tables of the art have a number of features in common; the chest or head area of the body is maintained in a stationary position at one end of the table, while the feet of the patient are gripped at the other end of the table. The feet are then pulled away from the rest of the body by mechanical means, such as ropes and pulleys, threaded adjustments, or the like. Most of these devices are relatively complex structures adapted to be used in the offices of doctors or chiropractors. For example, Warner U.S. Pat. No. 2,693,796 discloses a traction table having one portion of the top carrying ankle straps which moves away from the remainder of the top on a pair of rails and is driven by an electric motor. Similar devices are disclosed by Anderson, U.S. Pat. No. 2,590,670, Elsasser, U.S. Pat. No. 2,934,063, Goldman, U.S. Pat. No. 1,234,536, Lend U.S. Pat. No. 937,825, and Kubista, U.S. Pat. No. 1,642,158. In general, these tables are relatively complex devices which are designed to be monitored by another person during use by a patient.

Attempts have been made to produce relatively simple, and in some cases, portable, traction tables. For example, DeNise, U.S. Pat. No. 902,946 discloses a winch-operated pulley system whereby through turning a handle, the user can wind a rope which extends over a pulley system to a pair of straps which are bound around the user's ankles. A similar system which can be operated by the user himself is shown in Matthews, U.S. Pat. No. 2,798,481. In this apparatus, the user operates the crank located near his head which retracts a rope attached to a carriage over a pair of pulleys; the user's feet are fastened into boots which are mounted on the carriage. In the Matthews apparatus, the user must constantly apply pressure to the handle in order to effect stretching. In Gordon, U.S. Pat. No. 708,340, an ankle strap is attached to a longitudinally movable rod operated by a rack and pinion mechanism underneath the table. Roemer, U.S. Pat. No. 1,374,115, discloses a stretching apparatus for use with the body in a face-down position where the feet are maintained in boots and are urged away from the head portion of the body by means of a threaded jack in series combination with a tension spring. In general, the foregoing devices are somewhat bulky and difficult to use for an individual who wishes to use the device without assistance.

Accordingly, it is an object of the present invention to provide a traction table which is inexpensive to manufacture, and which is easily portable.

It is a further object of the invention to provide a portable traction table which is easy to assemble and disassemble, and which can be stored in a relatively small space under a bed or in a closet.

It is a further object of the invention to provide such an attraction table which is easy for an individual to use without assistance, providing ease of entry and exit into the apparatus, and which is easily and safely operated by the user.

It is a still further object of this invention to provide traction apparatus which can be folded to a storage position or unfolded to an operative position.

These and other objects are achieved by the device of the invention, a preferred embodiment of which is disclosed herein.

BRIEF SUMMARY OF THE INVENTION

In accordance with one embodiment of the invention, a portable traction apparatus comprises a base portion having first and second support members, at least one guide rail extending between the support members, a carriage having foot-restraining means for gripping a user's feet movable along the guide rail between the support members, a flat back-supporting member removably mounted on at least one of the support members having body restraining apparatus for holding the user's body in a fixed position on the member, and biasing means for selectively urging the carriage along the guide means. The body restraining means may include either shoulder straps having quick release buckles, or a head harness. The foot restraining means include a pair of spaced, padded, recesses in the carriage having a flexible strap extending over both recesses. The strap is tightened by means of a pivoted, long-handled rod which extends toward the user's body from the carriage and is easily accessible to the user.

BRIEF DESCRIPTION OF THE DRAWINGS

The invention is best understood with reference to the drawings, in which.

DETAILED DESCRIPTION OF PREFERRED EMBODIMENTS

Figure 1:
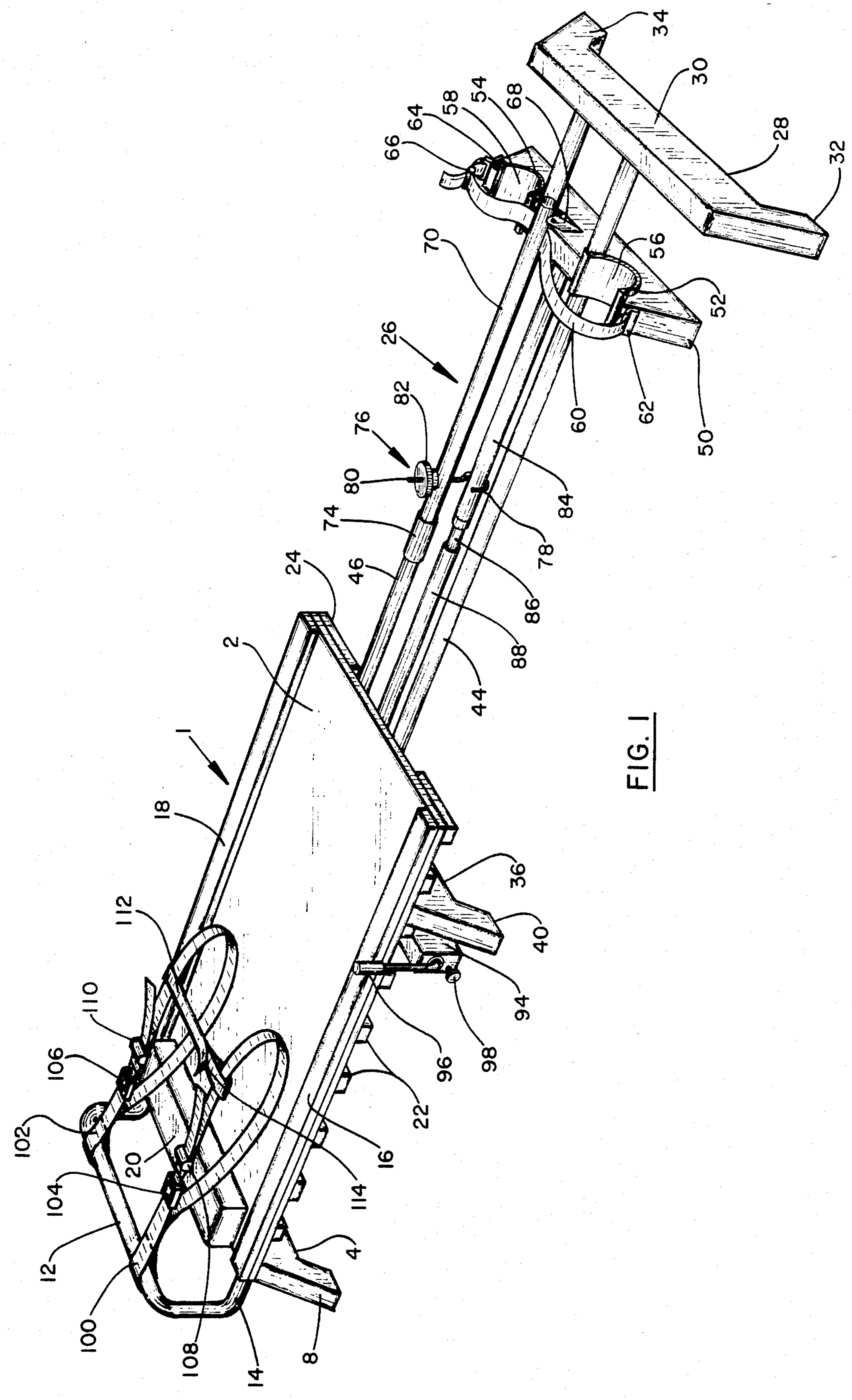
FIG. 1 is a perspective view of the entire portable traction apparatus of the invention in accordance with one embodiment.

Referring first to FIG. 1, portable traction apparatus 1 has a flat, horizontal back support member 2 consisting of a plywood board approximately 4′ long, 18″ wide, and ½″ thick. The back support member or panel is attached at its uppermost extremity by nuts and bolts (not shown) to a support member 4 which consists of a cast aluminum piece having a horizontal brace portion 6 and two legs 8 and 10. A tubular rail fabricated from 1″ aluminum or steel tubing has a pair of foot portions 14 which are frictionally mounted in an aligned pair of bores (not shown) in the rear surface of the horizontal brace portion 6 of support member 4. A pair of longitudinal stiffening rails 16 and 18 are fastened to the edges of the back-support panel for strength. A foam rubber pillow 20 is located at an upper portion of the back-support a panel to provide comfortable support for the user's head.

A series of equally spaced wooden spacers or lugs 22 and 24 (see bottom view FIG. 4) are attached to the longitudinal edges of the bottom surface of the back-support panel. These spacers are used to orient the support panel of its forward base support member, and to permit adjustment of the length of the entire traction table to fit users of different height.

A base portion 26 of the traction table, which is entirely separate from the previously described back-support panel, comprises a pair of spaced support members 28 and 36 fastened by a pair of tubular guide rails 44 and 46. Support member 28 at the forward, or foot, portion of the table consists of a cast aluminum member having a horizontal cross piece 30 supported at its ends by legs 32 and 34. Support member 36, located at a rearward portion of the base, is a similar member consisting of a horizontal cross piece 38 having legs 40 and 42 extending downwardly therefrom. The tubular guide rails 44 and 46 are press fit or threaded into bores (not shown) which extend partially through the thickness of the two support members.

A foot carriage 50 is slidably mounted on the guide rails 44 and 46, which extend through holes through the thickness of foot carriage 50. The foot carriage has a pair of spaced ankle recesses or stirrups 52 and 54 which have foam pad inserts 56 and 58, respectively, to provide comfort for the user's ankles. A strap 60 fabricated from 2″ woven nylon loops over the ankle stirrups, being fastened on either side of the carriage by strap fastening brackets 62 and 64. A conventional strap length adjustment device 66 permits a user to adjust the desired tension across his ankles.

Figure 3:
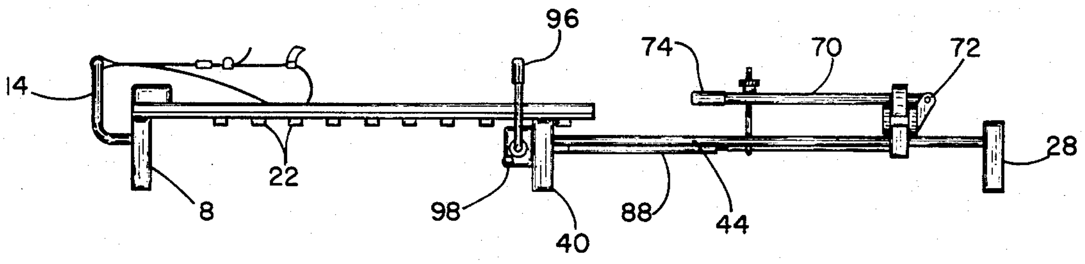
FIG. 3 is a side view thereof.

After placing his ankles in the stirrups, the user can tighten the strap across his ankles by pulling a long-handled tubular rod clamp 70, having as handle portion 74 at the end closest to the user's body, into the closed position as shown in FIGS. 1 and 3. Closing of the rod clamp forces the center portions of the strap downwardly to the upper surface of the carriage, tightening the strap over the ankles and cinching the strap to the upper surface of the foot carriage. The rod clamp is pivotally fastened to a U-shaped mounting bracket 68 which has a pair of arms forming a yoke extending upwardly from the carriage on either side of the rod tube. A threaded hinge pin 72 extends through the mounting bracket and across the diameter of the tube, fastening the rod to the bracket by permitting rotational movement around the pin. The elongate rod 70 extends rearwardly along the apparatus to be accessible to the user, and preferably is centrally located between the user's legs.

Figure 5:
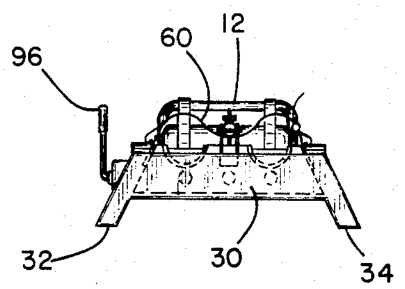
FIG. 5 is an end view thereof.

After the rod clamp has been pulled rearwardly from the released position shown in phantom in FIG. 5 into the closed position, the user may fasten the handle in the closed position by means of rod fastener 76. The rod fastener is a screw clamp having a hook portion 78 which engages the carriage driving tube 84 located immediately below the rod clamp, and an upper threaded portion 80 which is adapted to receive a threaded adjustment thumb wheel 82. After the hook has been placed around the tube 84, the thumb wheel is simply screwed down upon the upper portion of the rod clamp to hold the clamp in place.

Figure 4:
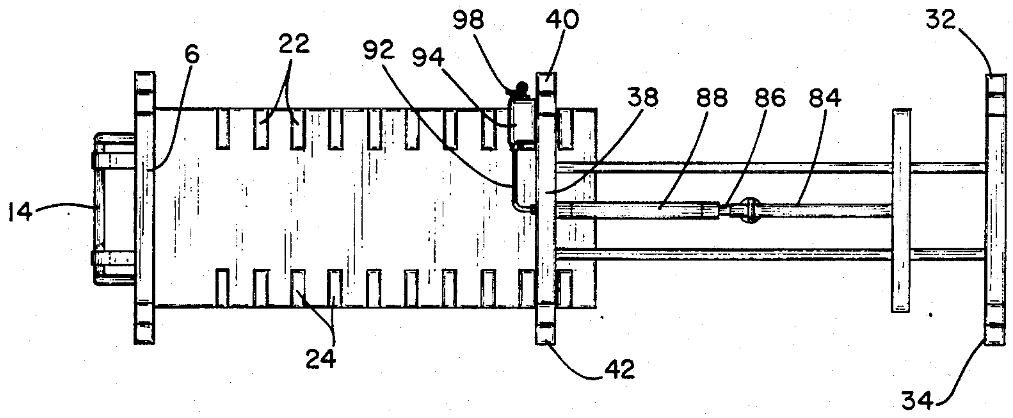
FIG. 4 is a bottom view thereof.
Figure 6:
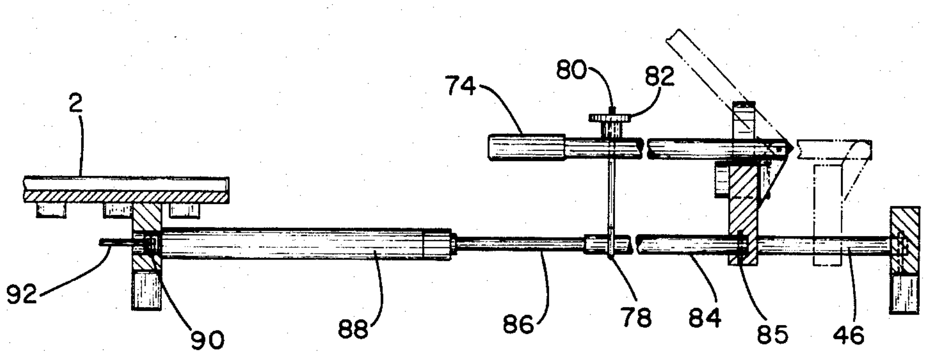
FIG. 6 is a partial side view thereof showing the movable portions of the device.

The foot carriage moves between the two support members 28 and 36 along the guide tubes 44 and 46. Movement of the foot carriage is controlled by a simple hydraulic pump system. A manually operated hydraulic pump 94 is mounted on the rear surface of base support member 36, and is actuated manually by pump handle 96. Pressure is exerted in the hydraulic cylinder by moving the handle 96 in a pumping fashion, and pressure in the cylinder is released by unscrewing the threaded pressure relief valve 98, permitting fluid to flow from the cylinder back into the fluid pump. As best seen in FIG. 4 and 6, hydraulic fluid passes from pump 94 through tube 92 into hydraulic cylinder 88, the threaded end 90 of which is engaged in a bore through the center portion of support member 36 as shown in FIG. 6. The ram portion 86 of the cylinder, which is forced outwardly as fluid is pumped into the cylinder, is threadedly engaged with a tube 84 that drives the carriage. As shown in FIG. 6, the tube 84 is press fit into a bore in the rear surface of the carriage, and is fixed into place by means of a screw 85. Hydraulic pump systems of the type shown are commercially available from many sources. Other drive systems for the carriage may be used with equal effectiveness; for example, a screw jack or ratchet-operated jack may be used with satisfactory results, and the invention should not be considered limited by the specific disclosure of a hydraulic drive system. An example of a suitable screw-jack device is a Joyce-Crindland Model WJ-500-12, which has a capacity of 500 lbs. pressure.

Figure 2:
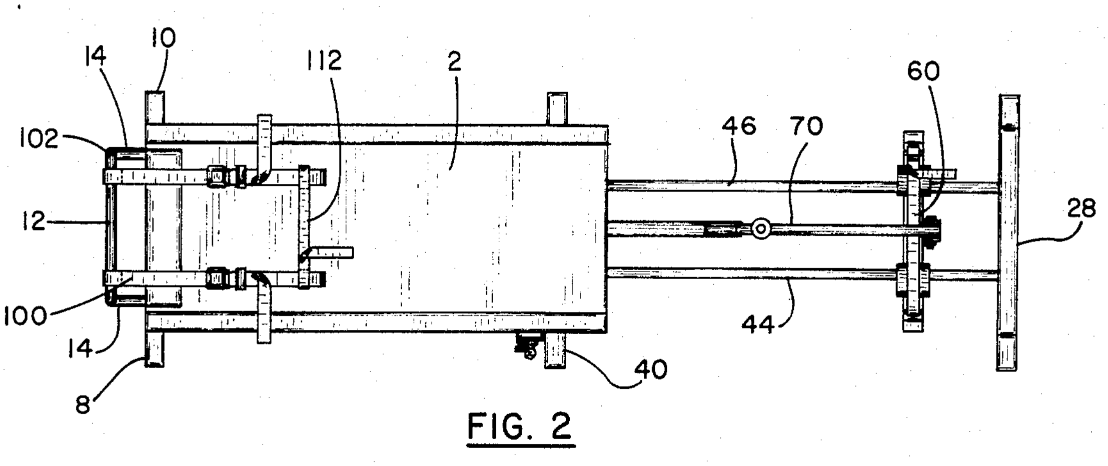
FIG. 2 is a top plan view thereof.
Figure 7:
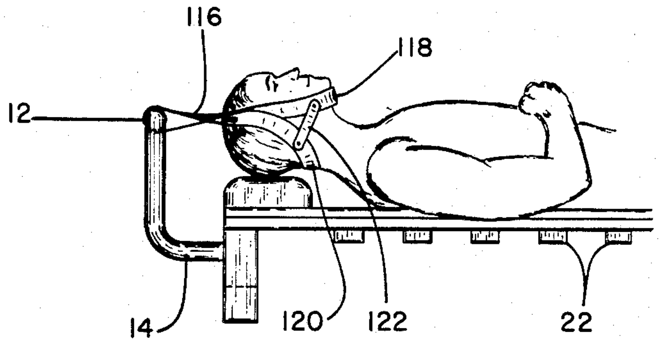
FIG. 7 is a partial side view of an embodiment of the invention showing the use of a head harness as a body restraining device.

To properly obtain tension on the spinal column, it is necessary to retain the upper portion of the body of the user in a fixed position relative to the back supporting panel 2. This may be accomplished by the use of either shoulder and chest restraining means, seen best in FIGS. 1 through 3, or through a head halter or harness as shown in FIG. 7. The shoulder restraining device consists of a pair of shoulder straps 100 and 102 attached to the mounting rail 12 and extending forwardly over the support panel 2. The straps are 2" wide nylon web members and are the same material as are used commonly in automobile seat belts. The straps are fastened by means of quick-release buckles 104 and 106, and are adjusted by length adjusters 108 and 110. The buckles and adjustment means are also conventional items which are commonly used as seat belts in automobiles or airplanes. A cross strap 112 is looped around the two shoulder straps and is fastened at the end 114 by means of conventional hook and loop fasteners, commonly known as "Velcro" fasteners. The cross strap provides additional stability to the shoulder strap and prevents the shoulder straps from sliding away from the body of the user.

An alternate method of retaining the upper end of the spine in fixed position on the support panel is shown in FIG. 7. A head halter 116 is mounted over the trail 12 and consists of a chin strap 118 and a rear portion 120 which extends around the rear base portion of the user's head as shown in the drawing. A pair of fastening straps 122 are located at each side of the halter and are removably attached by means of snap fasteners when the halter is in place on the head. The shoulder straps and head halter may be interchanged simply by removing the mounting rail 12, which is easily withdrawn from the bores in the support member 8 by grasping the leg portions 14 of the rail and pulling away from the support member. The straps may then be easily interchanged by sliding off the rail and replacing with the desired straps.

Because the thrust of the carriage-driving device (such as the hydraulic cylinder) is limited in the length of its extension, it may be necessary to adjust the position of the support panel 2 on the base depending on the height of the user. This is accomplished by lifting the forward portion of the panel and moving the panel longitudinally to set the desired pair of spacers 22 and 24 over the top of the rear support member 36 of the base. The panel is moved forwardly to accommodate shorter people, and rearwardly to accommodate taller people. If desired, indicia corresponding to the various heights of user may be placed along the side portion of the panel to assist the user in placing the panel over the base at the proper position.

In order to use the traction apparatus of the invention, the user first places the panel portion of the apparatus over the base as shown in FIG. 1 at the proper set of spaces to correspond to the user's height. The user then elevates the rod clamp 70 into the position shown in phantom in FIG. 6, thereby loosening the strap 60. He then sits on the support panel and places his feet in the ankle stirrups, sliding his feet underneath the strap. The handle 74 of the rod clamp is then pulled rearwardly, and screw clamp 76 set in place as shown in FIG. 1. The user lies back with his head on the pillow and buckles the two quick-connect shoulder straps 100 and 102, which have been preadjusted to the proper length. The cross strap 112 is then pulled across the user's chest and fastened into place by means of Velcro fasteners. The user then grasps the handle 96 of the hydraulic pump in his right hand and pumps the handle, thereby moving the carriage toward the front portion of the apparatus. The pressure on the carriage can be controlled easily by additional actuation of the hydraulic pump, or by releasing pressure through the use of the thumb screw valve 98, until the use of the apparatus has been completed. The body harness is then removed by disconnecting the cross strap and releasing the buckles on the shoulder straps, removing the hook clamp 76, and raising the rod clamp 70, thereby releasing the ankle straps. When not in use, the device can be easily stored in two sections, and if desired, the various rod and tube members may be removed for storage in a small area.

When completely fabricated, the back support panel 2 and pillow 20 will be covered by a decorative synthetic material such as Nauagahyde.

Figure 8:
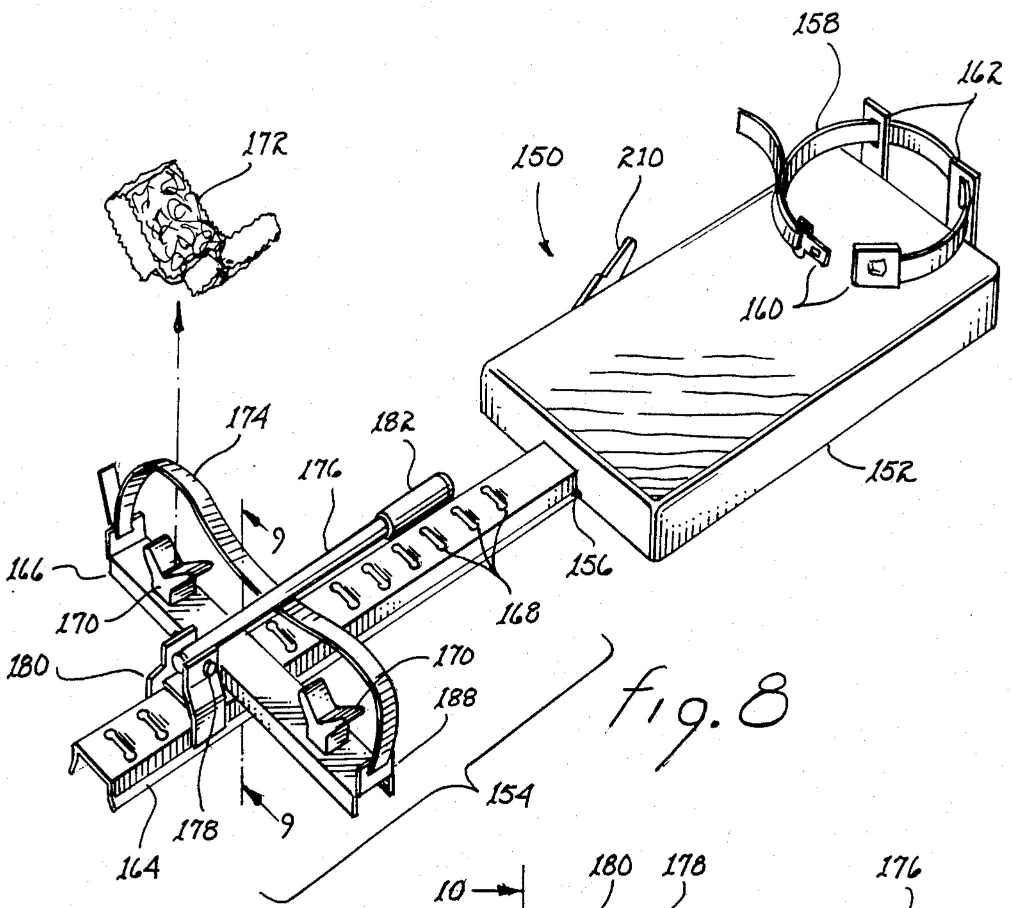
FIG. 8 is a perspective view of the entire traction apparatus in accordance with a further embodiment of the invention.

Portable traction apparatus in accordance with a further embodiment of the invention is illustrated in FIGS. 8–14. FIG. 8 illustrates apparatus 150 in perspective view. Apparatus 150 includes a first body supporting portion 152 and a second foot restraining portion 154. The two portions are joined by a hinge 156. The hinge between the two portions of the apparatus allow the apparatus to be folded for storage or carrying or to be extended, as illustrated in FIG. 8, for use as a traction apparatus.

Body portion 152 includes a generally flat back supporting member which is preferably of rectangular shape. The body support portion is preferably about 3–4 feet in length, about 16–24 inches is width, and has a thickness of about 2–4 inches. In the embodiment illustrated, the body support portion includes a chin strap 158 which can be fastened, as above, about the user's head and neck. Strap 158 is provided with a buckling mechanism 160 which is preferably a tongue and body mechanism of the seat belt variety. The strap 158 is attached to the body support portion through an upstanding frame 162.

The foot restraining portion includes a horizontal beam 164 which is preferably formed from a rigid metal channel. A foot support beam member 166 is adapted to ride on the beam. The beam is provided with a plurality of slots 168 which provide for the positioning of the foot support beam member along the beam. As explained more fully below, the length of the apparatus is roughly adjusted to a user's height by positioning the carriage at a desired location along the beam.

The foot support beam member is provided with two cradles or recesses 170 into which the user's feet, ankles, or lower legs are placed. In the following description, the operation the foot securing portion of the apparatus will be described in terms of holding the user's feet on the foot support beam member. This terminology is intended to encompass the securing of the user's feet, lower legs, or ankles. Recesses 170 are provided with a soft covering 172 which allow the feet to be comfortably secured against the recess. The covering 172 can be, for example, a foam material, sheep skin covering, or the like. An adjustable strap 174 extends from one end of the foot support beam member to the other. A user's feet are placed on the recesses 170 and underneath strap 174. The feet are secured in the recesses by pivotally mounted rod 176 which, in its lowered position as illustrated, clinches strap 174 down against the user's feet. Rod 176 is pivotally mounted to the carriage by a pin 178 which passes through a mounting bracket 180. Rod 176 is sufficiently long that a user can easily reach the handle 182 of the rod to raise the rod releasing his feet or lower the rod to secure his feet. Handle 182 is sufficiently weighted to hold the rod down against strap 174 to secure the user's feet against the recesses during the operation of the equipment.

Figure 9:
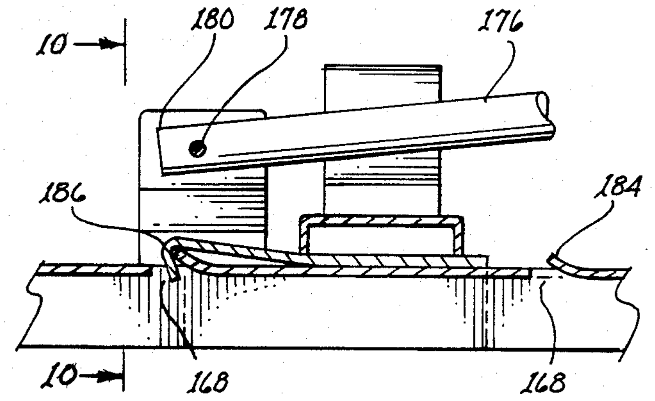
FIG. 9 shows a section through a portion of that apparatus which depicts a length adjustment arrangement.

FIG. 9 illustrates, in section, means for adjusting the length of the equipment to adapt to the user's height. Each of the spaced apart openings 168 in the top of beam 164 includes an upwardly protruding lip 184. Foot carriage 166 includes a mating member 186 on its lower surface. In use, the foot carriage is moved along the beam to the appropriate position, and the mating member 186 is brought into engagement with one of the protruding lips 184. The carriage is thus locked in the correct position, adjusting the length of the equipment by the engagement of the lip and the mating member.

Figure 10:
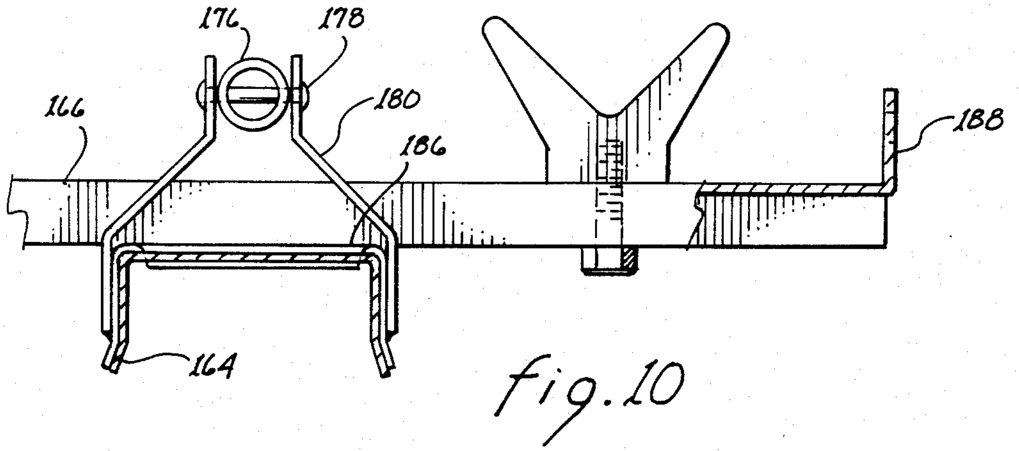
FIG. 10 shows a portion of the apparatus in end view.

FIG. 10 further illustrates a positioning of the foot support beam member on the horizontal beam 164. Strap 174 is attached to ratchet 188 mounted on the end of the foot support beam member.

Figure 11:
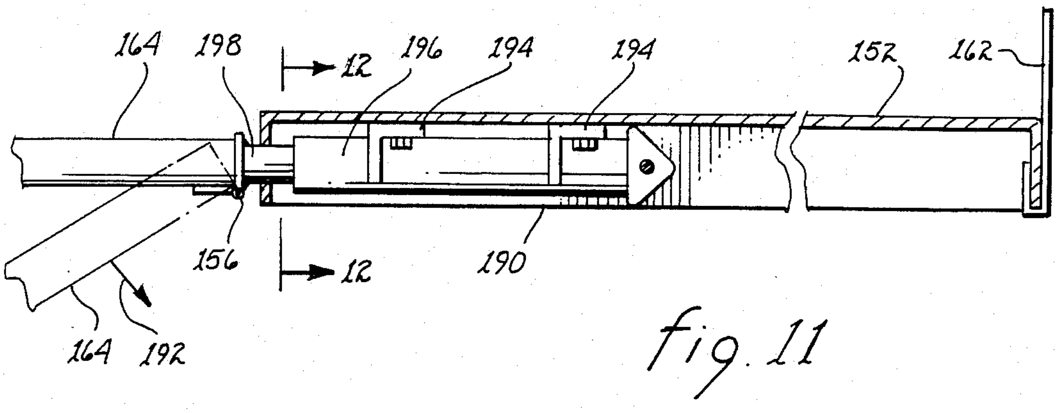
FIG. 11 illustrates, in section, a portion of the apparatus which allows incremental extension for traction.

FIGS. 11-15 illustrate a mechanism by which the length of the apparatus can be extended to apply traction to the user. FIG. 11 is a section through the body support portion of the apparatus showing the traction mechanism mounted thereunder. Traction mechanism 190 acts to move the beam 164 away from the body portion 152. Hinge 156 which join the body support portion 152 to the foot securing portion is moved away from the body support portion. This Figure also illustrates how the apparatus folds at hinge 156. Beam 164 is shown in an intermediate position indicated by 164 as it is swung to the folded position.

Figure 12:
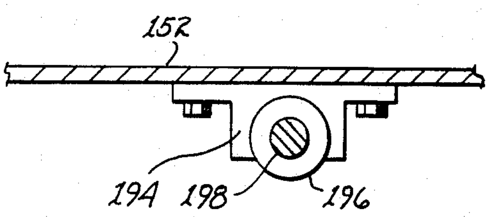
FIG. 12 illustrates a section through the incremental adjustment equipment.

The traction mechanism 190 is mounted to the underside of body support portion 152 by a pair of mounting brackets 194 as illustrated in cross-section in FIG. 12.

Figure 13:
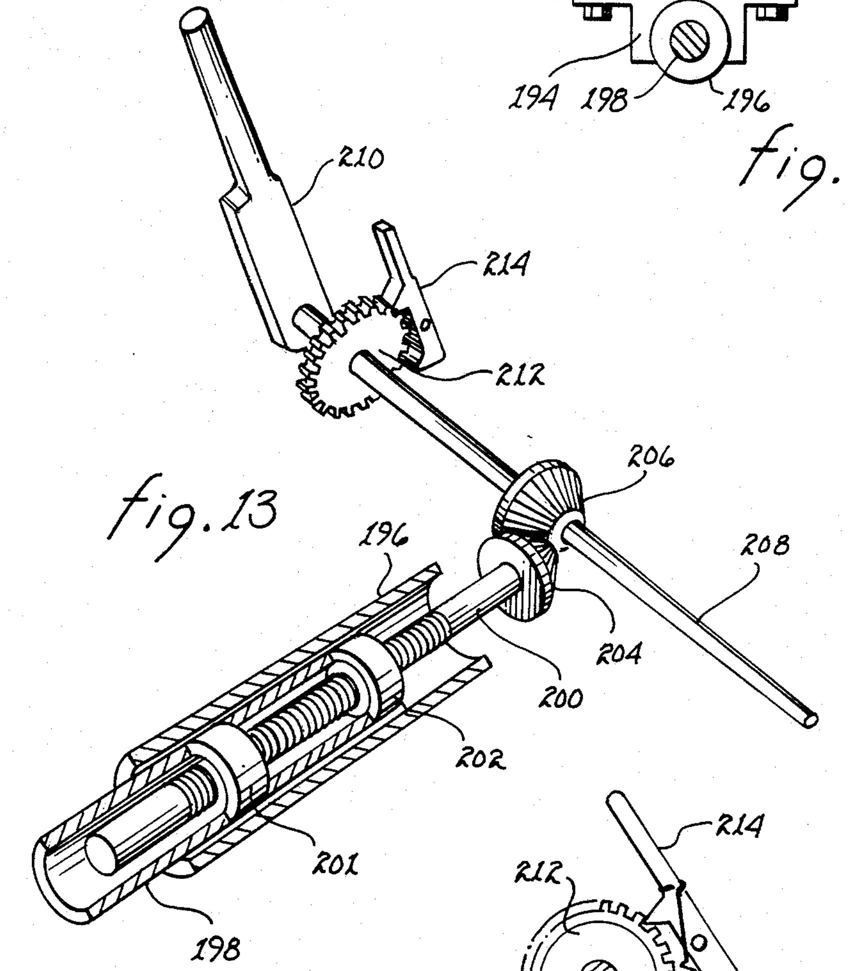
FIG. 13 illustrates, in partially cutaway perspective, the ratchet drive mechanism for incrementally lengthening the equipment.

As illustrated in these figures, as well as in FIG. 13, the traction mechanism includes a pair of concentric cylinders 196 and 198 is attached to the horizontal beam 164 by hinge 156. As inner cylinder 198 moves outwardly to lengthen the apparatus, traction is applied to the user.

A screw shaft 200 passes through the interior of the two cylinders and through two threaded fittings 201 and 202. The two threaded fittings, in turn, are coupled to the inner cylinder 198. Thus as screw shaft 200 rotates, threaded fittings 201 and 202 force the intercylinder to move relative to the position of the outer cylinder 196. A conical gear 204 is mounted on the end of screw shaft 200. Shaft 208 is mounted on the bottom side of body support portion 152 by a pair of brackets (not shown).

A ratchet mechanism 210 is mounted on the side of the body support portion in a position which is readily accessible to the user who is strapped to the body support portion. By operating the ratchet mechanism, the user causes shaft 208 to rotate, which, in turn, causes shaft 208 to rotate. The rotation of shaft 208, in turn, causes screw shaft 200 to rotate, causing the foot carriage securing the user's feet to be moved away from the body support portion. The user, by operating the ratchet mechanism, thus is able to controllably apply the appropriate amount of traction. A ratchet wheel 212 mounted near the end of shaft 208 together with a spring loaded pawl 214 maintains the amount of traction elected by the user. Following the traction treatment, the pawl is retracted allowing ratchet wheel 212 to rotate and releasing the traction.

Figure 14:
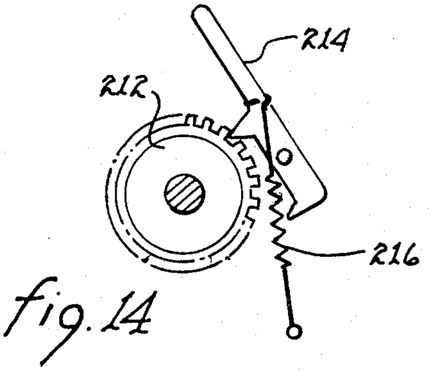
FIG. 14 illustrates, in side view, ratchet holding mechanism.

FIG. 14 illustrates in side view the ratchet wheel 212, pawl 214, and spring 216 which keeps the pawl in contact with the ratchet wheel until the pawl is retracted at the end of the treatment.

Two embodiments of the invention have been disclosed in detail. It is of course possible to interchange portions of the apparatus disclosed in the two embodiments. For example, the shoulder restraining straps illustrated in FIG. 1 can be used with the apparatus of FIG. 8. Likewise, the mechanism for applying traction can be interchanged between the two embodiments. The traction apparatus, in accordance with the second embodiment, is used in similar manner as described above with respect to the first embodiment.

Thus it is apparent that there has been provided, in accordance with the invention, portable traction apparatus which fully meets the objects and advantages set forth above. Two embodiments of the invention have been specifically described; in one embodiment portability is achieved through an apparatus which is separable into two demountable parts; in the other embodiment depicted, portability is achieved by hinging the lightweight and simple apparatus so that it can be folded into an easily transportable mode.

Many variations to the traction tables depicted will be immediately apparent to those skilled in the art, and therefore the invention should not be considered limited by the descriptions of the specific embodiments thereof set forth herein. Accordingly, the invention should be limited only by the scope of the following claims.

What is claimed is:

1. Portable traction apparatus, comprising:

a first body supporting portion;

a second foot restraining portion;

hinge means joining said first and second portions and allowing said apparatus to be extended for use or folded for storage;

means for securing a user's head to said first portion;

means for securing a user's feet to said second portion, said means for securing a user's feet comprises a foot support beam member, recesses in said foot support beam member adapted for receiving a user's feet, and strap means for securing the user's feet in said recesses;

means for adjusting the length of said apparatus;

means accessible to the user for further lengthening said apparatus to apply traction to a user fastened thereto, said means accessible to the user for applying traction comprises a ratchet operated screw assembly; and means for tightening said strap means for securing the user's feet, said means for tightening comprises a pivoted rod centrally mounted on said foot support beam member movable between a release position and a closed position wherein said rod in said closed position clinches said strap means for securing the user's feet toward said foot support beam member between said recesses.

2. A portable and folding traction apparatus comprising:

a first body supporting portion to which a user's head can be secured by straps;

a second foot securing portion to which a user's feet can be secured, said second foot securing portion has a tightening means for tightening said strap means over the user's feet which comprises a shaft pivotally attached to said carriage and positioned to clinch said strap means across the user's feet when said shaft is in a lowered position said shaft extending from said carriage toward said body supporting position and having a handle at the end thereof accessible to the user;

a horizontal beam upon which said second foot securing portion is mounted, said horizontal beam hinged to said first body supporting portion;

the hinged connection allowing said beam and foot securing portion to be extended for use or folding for storage;

a plurality of positions spaced along said beam at which said foot securing portion can be attached to said beam; and ratchet means accessible to said user for moving said beam and said foot securing portion away from said body supporting portion to apply traction to a user attached thereto.

3. Portable traction apparatus, comprising:

a first body supporting portion;

a second foot restraining portion;

hinge means joining said first and second portions and allowing said apparatus to be extended for use or folded for storage;

means for securing a user's head to said first portion;

means for securing a user's feet to said second portion, said means for securing a user's feet comprises a foot support beam member, recesses in said foot support beam member adapted for receiving a user's feet, and strap means for securing the user's feet in said recesses;

means for adjusting the length of said apparatus;

means accessible to the user for further lengthening said apparatus to apply traction to a user fastened thereto; and means for tightening said strap means for securing the user's feet, said means for tightening comprises a pivoted rod centrally mounted on said foot support beam member movable between a release position and a closed position wherein said rod in said closed position clinches said strap means for securing the user's feet toward said foot support beam member between said recesses.

4. The apparatus of claim 3 wherein said pivoted rod comprises a weighted handle of sufficient weight to hold said rod in said closed position.

5. The apparatus of claim 4 wherein said means for adjusting the length of the apparatus comprises:

a plurality of spaced apart openings along the length of a beam member, each of said openings having an upwardly extending lip; and a mating member coupled to said foot support beam member for mating with said lip of a selected one of said plurality of spaced apart openings.

6. The apparatus of claim 5 wherein said means accessible to the use comprises:

means coupled to said first body supporting portion and to aid hinge means for disposing said hinge means and a horizontal beam member a distance away from said first body supporting portion.

* * * * *